(12) United States Patent
Lamego et al.

(10) Patent No.: US 12,343,108 B2
(45) Date of Patent: *Jul. 1, 2025

(54) CLOUD-BASED PHYSIOLOGICAL MONITORING SYSTEM

(71) Applicant: Willow Laboratories, Inc., Irvine, CA (US)

(72) Inventors: Marcelo M. Lamego, Cupertino, CA (US); Abraham Mazda Kiani, San Juan Capistrano, CA (US); Don Sanders, Irvine, CA (US); Jeroen Poeze, Rancho Santa Margarita, CA (US); Massi Joe E Kiani, Laguna Niguel, CA (US); Anthony Amir Davia, Laguna Beach, CA (US)

(73) Assignee: Willow Laboratories, Inc., Irvine, CA (US)

( * ) Notice: Subject to any disclaimer, the term of this patent is extended or adjusted under 35 U.S.C. 154(b) by 162 days.

This patent is subject to a terminal disclaimer.

(21) Appl. No.: 16/570,426

(22) Filed: Sep. 13, 2019

(65) Prior Publication Data

US 2020/0000338 A1 Jan. 2, 2020

Related U.S. Application Data

(63) Continuation of application No. 14/203,243, filed on Mar. 10, 2014, now Pat. No. 10,456,038.
(Continued)

(51) Int. Cl.
*A61B 5/00* (2006.01)
*A61B 5/1455* (2006.01)
*G16H 50/30* (2018.01)

(52) U.S. Cl.
CPC ........ *A61B 5/0022* (2013.01); *A61B 5/14551* (2013.01); *G16H 50/30* (2018.01); *A61B 5/7235* (2013.01)

(58) Field of Classification Search
CPC . A61B 5/0022; A61B 5/14551; A61B 5/7235; A61B 5/0004; A61B 5/0205; A61B 5/7275; G06F 19/3431; G06F 19/3418
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |

(Continued)

FOREIGN PATENT DOCUMENTS

| | | |
|---|---|---|
| EP | 2 278 508 | 1/2011 |
| WO | WO 2012/099534 | 7/2012 |
| WO | WO 2014/149781 | 9/2014 |

OTHER PUBLICATIONS

US 2022/0192529 A1, 06/2022, Al-Ali et al. (withdrawn)
(Continued)

*Primary Examiner* — Eugene T Wu
(74) *Attorney, Agent, or Firm* — Knobbe, Martens, Olson & Bear, LLP

(57) ABSTRACT

A cloud-based physiological monitoring system has a sensor in communications with a living being so as to generate a data stream generally responsive to a physiological condition of the living being. A monitor receives the data stream from the sensor and transmits the data stream to a cloud server. The cloud server processes the data stream so as to derive physiological parameters having values responsive to the physiological condition. The cloud server derives a medical index based upon a combination of the physiological parameters. The cloud server communicates the medical index to the monitor, which displays the medical index.

18 Claims, 11 Drawing Sheets

Related U.S. Application Data

(60) Provisional application No. 61/922,861, filed on Jan. 1, 2014, provisional application No. 61/885,491, filed on Oct. 1, 2013, provisional application No. 61/841,346, filed on Jun. 30, 2013, provisional application No. 61/801,464, filed on Mar. 15, 2013.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,565,976 A | 10/1996 | Fieggen et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,648,820 B1 | 11/2003 | Sarel |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |

(56) References Cited

U.S. PATENT DOCUMENTS

| | | |
|---|---|---|
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |

(56) References Cited

U.S. PATENT DOCUMENTS

| | | |
|---|---|---|
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |

(56) References Cited

U.S. PATENT DOCUMENTS

| | | | |
|---|---|---|---|
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |

(56) References Cited

U.S. PATENT DOCUMENTS

| | | |
|---|---|---|
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |

(56) References Cited

U.S. PATENT DOCUMENTS

| | | |
|---|---|---|
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Ai-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |

(56) References Cited

U.S. PATENT DOCUMENTS

| | | |
|---|---|---|
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0034289 A1 | 2/2004 | Teller et al. |
| 2004/0106163 A1 | 6/2004 | Workman, Jr. et al. |
| 2005/0055276 A1 | 3/2005 | Kiani et al. |
| 2005/0171444 A1* | 8/2005 | Ono ................. A61B 5/0002 |
| | | 600/490 |
| 2005/0228298 A1* | 10/2005 | Banet ................. A61B 5/021 |
| | | 600/323 |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0225614 A1* | 9/2007 | Naghavi ................. A61B 5/01 |
| | | 600/549 |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0043222 A1* | 2/2009 | Chetham ............. A61B 5/4878 |
| | | 600/547 |
| 2009/0093687 A1 | 4/2009 | Telfort et al. |
| 2009/0095926 A1 | 4/2009 | MacNeish, III |
| 2009/0118628 A1* | 5/2009 | Zhou ................. A61B 5/1075 |
| | | 600/499 |
| 2009/0149724 A1* | 6/2009 | Mark ................. A61B 5/412 |
| | | 600/301 |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0069725 A1* | 3/2010 | Al-Ali ................. A61B 5/7425 |
| | | 600/301 |
| 2010/0076787 A1* | 3/2010 | Naylor ................. G16H 15/00 |
| | | 705/3 |
| 2010/0099964 A1* | 4/2010 | O'Reilly ............. A61B 5/14551 |
| | | 600/323 |
| 2010/0217099 A1 | 8/2010 | LeBoeuf et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0034209 A1 | 2/2011 | Rubinsky et al. |
| 2011/0040197 A1* | 2/2011 | Welch ................. A61B 5/002 |
| | | 600/509 |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0201905 A1* | 8/2011 | Spencer ................. A61B 5/412 |
| | | 600/301 |
| 2011/0208015 A1 | 8/2011 | Welch et al. |
| 2011/0230733 A1 | 9/2011 | Al-Ali |
| 2011/0257489 A1* | 10/2011 | Banet ................. A61B 5/0809 |
| | | 600/301 |
| 2012/0123231 A1 | 5/2012 | O'Reilly |
| 2012/0145152 A1* | 6/2012 | Lain ................. A61M 16/026 |
| | | 128/204.23 |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0144136 A1* | 6/2013 | Rymut ................. A61B 5/4875 |
| | | 600/310 |
| 2013/0231947 A1* | 9/2013 | Shusterman ....... A61B 5/02055 |
| | | 705/2 |
| 2013/0243021 A1 | 9/2013 | Siskavich |
| 2013/0296672 A1 | 11/2013 | O'Neil et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0366507 A1 | 12/2015 | Blank |
| 2016/0029932 A1 | 2/2016 | Ai-Ali |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0103598 A1 | 4/2016 | Al-Ali et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0367173 A1 | 12/2016 | Dalvi et al. |
| 2017/0000394 A1 | 1/2017 | Al-Ali et al. |
| 2017/0014083 A1 | 1/2017 | Diab et al. |
| 2017/0024748 A1 | 1/2017 | Haider |
| 2017/0042488 A1 | 2/2017 | Muhsin |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0086723 A1 | 3/2017 | Al-Ali et al. |
| 2017/0143281 A1 | 5/2017 | Olsen |
| 2017/0147774 A1 | 5/2017 | Kiani |

(56) References Cited

U.S. PATENT DOCUMENTS

| | | |
|---|---|---|
| 2017/0156620 A1 | 6/2017 | Al-Ali et al. |
| 2017/0173632 A1 | 6/2017 | Al-Ali |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0311891 A1 | 11/2017 | Kiani et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0253947 A1 | 9/2018 | Muhsin et al. |
| 2018/0256087 A1 | 9/2018 | Al-Ali et al. |
| 2018/0285094 A1 | 10/2018 | Housel et al. |
| 2018/0289325 A1 | 10/2018 | Poeze et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |

(56) References Cited

U.S. PATENT DOCUMENTS

| | | |
|---|---|---|
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0252046 A1 | 8/2024 | Jansen et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |

OTHER PUBLICATIONS

US 2024/0016391 A1, 01/2024, Lapotko et al. (withdrawn)

Xiaomao Fan et al., "HCloud: A novel application-oriented cloud platform for preventive healthcare," Cloud Computing Technology and Science (CLOUDCOM), Dec. 3, 2012, pp. 705-710.

Chung-Ping Young et al., "A portable multi-channel behavioral state and physiological signal monitoring system," May 13, 2012, pp. 2687-2691.

International Search Report and Written Opinion issued in International Application No. PCT/US2014/020903 dated Dec. 5, 2014.

\* cited by examiner

| Index | Hgb | BUN | Cr | PVI | BP |
|---|---|---|---|---|---|
| Dehydration | ← | ← | ← | ← | → |

FIG. 8A

| Index | Hgb | BUN | Cr | PVI | BP |
|---|---|---|---|---|---|
| Renal Insufficiency | → | ⇈ | ← to ⇇ | → | ← |

FIG. 8B

| Index | Hgb | BUN | Cr | PVI | BP |
|---|---|---|---|---|---|
| Over-hydration | → | → | ↔ | → | ← |

FIG. 8C

| Index | Hgb | BUN | Cr | PVI | BP |
|---|---|---|---|---|---|
| Gastrointestinal Bleeding | → | ← | ↔ | ← | ↔ to → |

FIG. 8D

| Index | Hgb | BUN | Cr | PVI | BP |
|---|---|---|---|---|---|
| Congestive Heart Failure Exacerbation | ↔ to → | ↔ to → | ↔ to ← | → | ↔ to ← |

FIG. 8E

| Index | Chol | HDL | Chol/HDL | Trig | BP |
|---|---|---|---|---|---|
| Cardiovascular Risk | ← | → | ← | ← | ← |

FIG. 8F

| Index | Na+ | K+ | CO2 | Cl- | Glu | Ca | BUN | Cre | ALP | ALT | AST | Tbil |
|---|---|---|---|---|---|---|---|---|---|---|---|---|
| Diabetic ketoacidosis | ↓ | ↕, mostly ↓ | ↓ | ↓ | ↑↑ | ↔ to ↓ | ← | ← | ↕ | ↕ | ↕ | ↕ |
| Asthma Exacerbation | ↕ | ↕ | ↕ | ↕ | ↕ | ↕ | ↕ | ↕ | ↕ | ↕ | ↕ | ↕ |
| Acute Upper Resp Infection | ↕ | ↕ | ↓ | ↕ | ↕ | ← | ↕ | ↕ | ↕ | ↕ | ↕ | ↕ |
| Chronic Renal Insufficiency | ↔ to ↓ | ↕ | ↕ | ↔ to ↓ | ↔ to ↑ | ↕ | ↑↑ | ↑↑ | ↔ to ↑ | ↑↑ | ↑↑ | ↕ |
| Liver Cirrhosis/Failure | ↔ to ↓ | ↔ to ↑ | ↔ to ↑ | ↕ | ↔ to ↓ | ← | ↔ to ↑ | ↔ to ↑ | ↕ | ↕ | ← | ← |
| Chronic Hypertension | ↕ | ↕ | ↕ | ↕ | ↕ | ↕ | ↕ | ↕ | ← | ↔ to ↑ | ↕ | ↕ |
| Hyperlipidemia | ↕ | ↕ | ↕ | ↕ | ↕ | ↕ | ↕ | ↕ | ↕ | ↔ to ↑ | ↔ to ↑ | ↕ |
| Acute cholecystitis | ↕ | ↕ | ↕ | ↕ | ↕ | ↕ | ↕ | ↕ | ← | ↕ | ↕ | ↕ |
| Evolving MI | ↕ | ↕ | ↕ | ↕ | ↕ | ↕ | ↑↑ | ← | ↕ | ↔ to ↑ | ↔ to ↑ | ↑↑ |
| Dehydration/heat stroke | ← | ↔ to ↑ | ← | ← | ↕ | ↕ | ↕ | ← | ↕ | ↕ | ↕ | ↔ to ↑ |

| | Alb | TP | Chol | HDL | Trig | LDL | VLDL | SpO2 | BP | RR | Temp | ECG/HR |
|---|---|---|---|---|---|---|---|---|---|---|---|---|
| | ↕ | ↕ | ↕ | ↕ | ↑ or ↕ | ↕ | ↕ | ↔ to ↓ | ↓ | ← | ↓ or ↑ | ← |
| | ↕ | ↕ | ↕ | ↕ | ↕ | ↕ | ↕ | ↓ | ↔ to ↑ | ← | ↕ | ← |
| | ↕ | ↕ | ↕ | ↕ | ↕ | ↕ | ↕ | ↔ to ↓ | ↕ | ↑ or ↕ | ← | ↑ or ↕ |
| | → | ↕ | ↔ to ↑ | ↔ to ↓ | ↔ to ↓ | ↔ to ↓ | ↔ to ↓ | ↕ | ↔ to ↑ | ↑ or ↕ | ↕ | ↔, may see peaked T waves |
| | ↕ | → | ↕ | ↕ | ← | ← | ← | ↕ | ↑↑ | ↑ or ↕ | ↕ | varied depending on extent of disease |
| | ↕ | ↕ | ← | ↕ | ↕ | ↕ | ↕ | ↕ | ↔ to ↑ | ↕ | ← | LVH, possible evidence of old MI |
| | ↕ | ↕ | ↕ | ↕ | ↔ to ↑ | ↔ to ↓ | ↔ to ↓ | ↕ | ↔ to ↑ | ↔ to ↑ | ↕ | ↔, may see Q waves |
| | ↕ | ↕ | ↕ | ↕ | ↕ | ↕ | ↕ | ↔ to ↓ | ↔ to ↑ | ↔ to ↑ | ↔ to ↑ | ← |
| | ↕ | ↕ | ↕ | ↕ | ↕ | ↕ | ↕ | ↔ to ↓ | → | ↔ to ↑ | ↔ to ↑ | ↑, ST segment elevation, poor R wave progression |
| | ← | ← | ↕ | ↕ | ↕ | ↕ | ↕ | ↕ | ↕ | ↕ | ↕ | ← |

FIG. 9

CLOUD-BASED PHYSIOLOGICAL MONITORING SYSTEM

PRIORITY CLAIM AND REFERENCE TO RELATED APPLICATIONS

The present application is a continuation of U.S. patent application Ser. No. 14/203,243, filed Mar. 10, 2014, titled Cloud-Based Physiological Monitoring System, which application claims priority benefit under 35 U.S.C. § 119(e) to U.S. Provisional Patent Application Ser. No. 61/801,464, filed Mar. 15, 2013, titled Cloud-Based Blood Glucose Monitoring System; U.S. Provisional Patent Application Ser. No. 61/841,346, filed Jun. 30, 2013, titled Cloud-Based Monitoring System; U.S. Provisional Patent Application Ser. No. 61/885,491, filed Oct. 1, 2013, titled Cloud-Based Monitoring System; and U.S. Provisional Patent Application Ser. No. 61/922,861, filed Jan. 1, 2014, titled Cloud-Based Physiological Index Monitoring System; all of the above-referenced provisional patent applications are hereby incorporated in their entireties by reference herein.

BACKGROUND OF THE INVENTION

Medical device manufacturers are continually increasing the processing capabilities of physiological monitors that process signals based upon the attenuation of light by a tissue site. In general, such physiological monitoring systems include one or more optical sensors that irradiate a tissue site and one or more photodetectors that detect the optical radiation after attenuation by the tissue site. The sensor communicates the detected signal to a physiological monitor, which removes noise and preprocesses the signal. Advanced signal processors then perform time domain and/or frequency domain processing to determine blood constituents and other physiological parameters.

Manufacturers have advanced basic pulse oximeters from devices that determine measurements for blood oxygen saturation ("$SpO_2$"), pulse rate ("PR") and plethysmographic information to read-through-motion oximeters and to co-oximeters that determine measurements of many constituents of circulating blood. For example, Masimo Corporation of Irvine Calif. ("Masimo") manufactures pulse oximetry systems including Masimo SET® low noise optical sensors and read through motion pulse oximetry monitors for measuring $SpO_2$, pulse rate (PR) and perfusion index (PI). Masimo optical sensors include any of Masimo LNOP®, LNCS®, SofTouch™ and Blue™ adhesive or reusable sensors. Masimo pulse oximetry monitors include any of Masimo Rad-8®, Rad-5®, Rad®-5v or SatShare® monitors. Such advanced pulse oximeters and low noise sensors have gained rapid acceptance in a wide variety of medical applications, including surgical wards, intensive care and neonatal units, general wards, home care, physical training and virtually all types of monitoring scenarios.

Many innovations improving the measurement of blood constituents are described in at least U.S. Pat. Nos. 6,770,028; 6,658,276; 6,157,850; 6,002,952; 5,769,785 and 5,758,644, which are assigned to Masimo and are incorporated in their entireties by reference herein. Corresponding low noise optical sensors are disclosed in at least U.S. Pat. Nos. 6,985,764; 6,088,607; 5,782,757 and 5,638,818, assigned to Masimo and hereby incorporated in their entireties by reference herein.

Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Advanced blood parameter monitors further include Masimo Rainbow 4D™ DC sensors and Masimo Pronto® and Pronto-7® monitors for noninvasive and quick spot checking of total hemoglobin (SpHb®, $SpO_2$, pulse rate and perfusion index).

Advanced parameter measurement systems may also include acoustic monitoring such as acoustic respiration rate (RRa™) using a Rainbow Acoustic Sensor™ and Rad-87™ monitor, available from Masimo. An advanced parameter measurement system that includes acoustic monitoring is described in U.S. Pat. Pub. No. 2010/0274099, filed Dec. 21, 2009, titled Acoustic Sensor Assembly, assigned to Masimo and incorporated in its entirety by reference herein.

Innovations relating to other advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, CA (Cercacor) and all incorporated in their entireties by reference herein.

SUMMARY OF THE INVENTION

One aspect of a cloud-based physiological monitoring system is a sensor in communications with a living being so as to generate a data stream generally responsive to a physiological condition of the living being. A monitor receives the data stream from the sensor and transmits the data stream to a cloud server. The cloud server processes the data stream so as to derive parameters having values responsive to the physiological condition. The cloud server derives a medical index based upon a combination of the parameters. The cloud server communicates the medical index to the physiological monitor and the physiological monitor displays the medical index.

In an embodiment, the cloud-based physiological monitoring system sensor comprises an optical sensor and the parameters comprise a blood constituent parameter. The parameters comprise a plethysmograph waveform parameter. A blood pressure sensor is in communications with the living being, and a blood pressure monitor receives a blood pressure data stream from the blood pressure sensor and transmits the blood pressure data stream to the cloud server. The cloud server processes the blood pressure data stream so as to derive a blood pressure parameter having a blood pressure value responsive to the physiological condition and the parameters further comprise the blood pressure parameter.

In various other embodiments, the medical index is based upon trends of the combination of the parameters. The blood constituents include Hgb, BUN and Cr. The medical index relates to at least one of hydration, cardiovascular risk and renal insufficiency. In a particular embodiment, the medical index relates to at least one of dehydration, over hydration, gastrointestinal bleeding and congestive heart failure exacerbation.

Another aspect of a cloud-based physiological monitoring system comprises generating sensor data generally responsive to a physiological phenomenon of a living being, communicating the sensor data to a local medical device and transmitting the sensor data from the local medical device to a remote cloud server. The system further comprises processing the sensor data at the cloud server so as to derive parameters having values responsive to the physiological phenomenon and trending the parameters at the cloud server so as to derive a medical index responsive to the parameters, where the medical index indicates a medical condition. The system additionally comprises communicating the medical index to the local medical device and displaying the medical index on the local medical device.

In various embodiments, cloud-based physiological monitoring system comprises generating second sensor data generally responsive to a second physiological phenomenon of a living being, communicating the second sensor data to a second local medical device and transmitting the second sensor data from the second local medical device to the remote cloud server. The system further comprises processing the second sensor data at the cloud server so as to derive a second parameter having values responsive to the second physiological phenomenon and trending the second parameter with at least one of the parameters at the cloud server so as to improve the efficacy of the medical index. In various other embodiments, generating sensor data comprises optically-deriving data responsive to pulsatile blood flow. Generating second sensor data comprises air-cuff-deriving data responsive to blood pressure. The system further comprises time frame matching the sensor data and the second sensor data at the cloud server. In a particular embodiment, displaying the medical index comprises indicating hydration on a smart cellular telephone.

A further aspect of a cloud-based physiological monitoring system comprises a physiological monitor in remote communications with a cloud server, where the physiological monitor inputs sensor data responsive to a physiological condition of a user. The cloud server is in remote communications with the physiological monitor so as to upload the sensor data. The cloud server executes signal processing algorithms so as to derive a physiological parameter from the sensor data. The cloud server downloads the physiological parameter to the physiological monitor for display to user.

In various embodiments, the physiological monitor has an online application that executes if the cloud server is available and, if so, the online application inputs sensor data from a physiological sensor in communications with the physiological monitor, transmits the sensor data to the cloud server, receives a parameter value that the cloud server derives from the sensor data and displays the parameter value on the physiological monitor. The physiological monitor has an offline application that executes if the cloud server is unavailable and, if so, the offline application inputs sensor data from a physiological sensor in communications with the physiological monitor, calculates a parameter value from the sensor data and displays the parameter value on the physiological monitor.

In various further embodiments, the online application performs an initial blood glucose calibration phase of the physiological monitor that comprises repeated blood sample data derived from a strip reader over an initial calibration period of several weeks and repeated optical sensor data corresponding to the blood sample data. The blood sample data and the sensor data are transmitted to the cloud server and the cloud server correlates the blood sample data and the sensor data during the initial calibration stage. The online application further performs an end blood glucose calibration phase of the physiological monitor that comprises optical sensor data occasionally interspersed with blood sample data. The sensor data and occasional blood sample data are transmitted to the cloud server, which updates the calibration as needed.

In additional embodiments, a share user establishes a receive user who is allowed to view the share user's medical information. A share ID is associated with the share user's physiological monitor. A receive ID is associated with the receive user's physiological monitor. The cloud server associates the share ID with the receive ID. The cloud server encrypts the share user's medical information according to a share key based upon the share ID. The cloud server generates a decryption key based upon the receive ID. The cloud server transmits the encrypted medical information and share key to the share user. The cloud server transmits the receive key to the receive user. The share user posts the encrypted medical information to a public website, the receive user downloads the encrypted medical information and the receive user decrypts the medical information using the receive key.

BRIEF DESCRIPTION OF THE DRAWINGS

FIG. 8A-F are medical index tables illustrating trends in blood-related parameters, plethysmograph waveform features and blood pressure that are indicative of dehydration, renal insufficiency, over-hydration, gastrointestinal bleeding, congestive heart failure exacerbation and cardiovascular risk, respectively.

FIG. 9 is a comprehensive medical index table illustrating trends in various physiological measurements, including blood-constituents and oxygen saturation, blood pressure, respiration rate (RR), temperature and heart-related parameters including heart rate (HR) and electrocardiogram (ECG) waveform features indicative of various physiological conditions, maladies and diseases.

DETAILED DESCRIPTION OF THE PREFERRED EMBODIMENTS

Figure 1A:
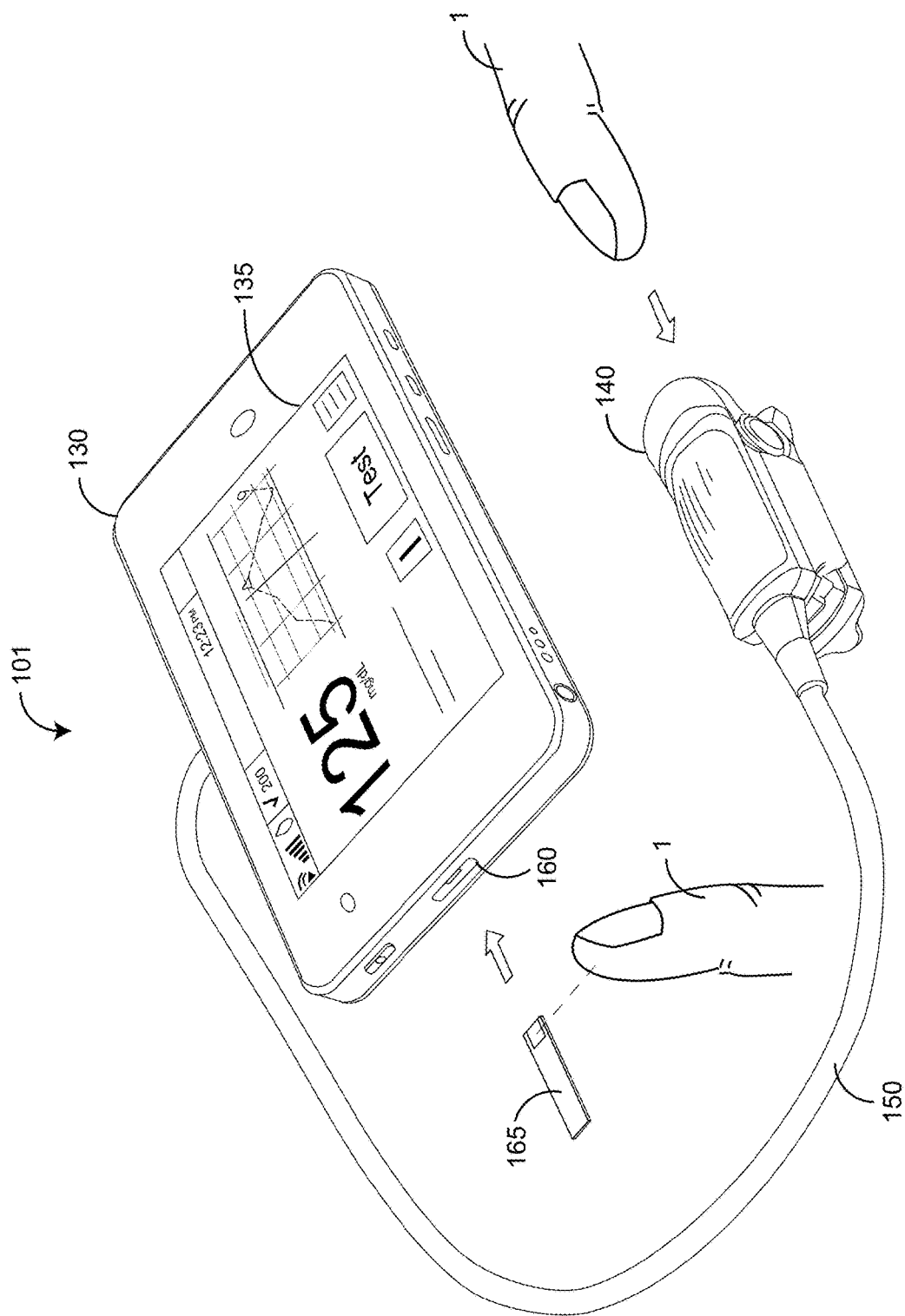
FIGS. 1A-B are perspective views of cloud-based monitoring systems that are capable of blood parameter and blood pressure monitoring.
Figure 1B:
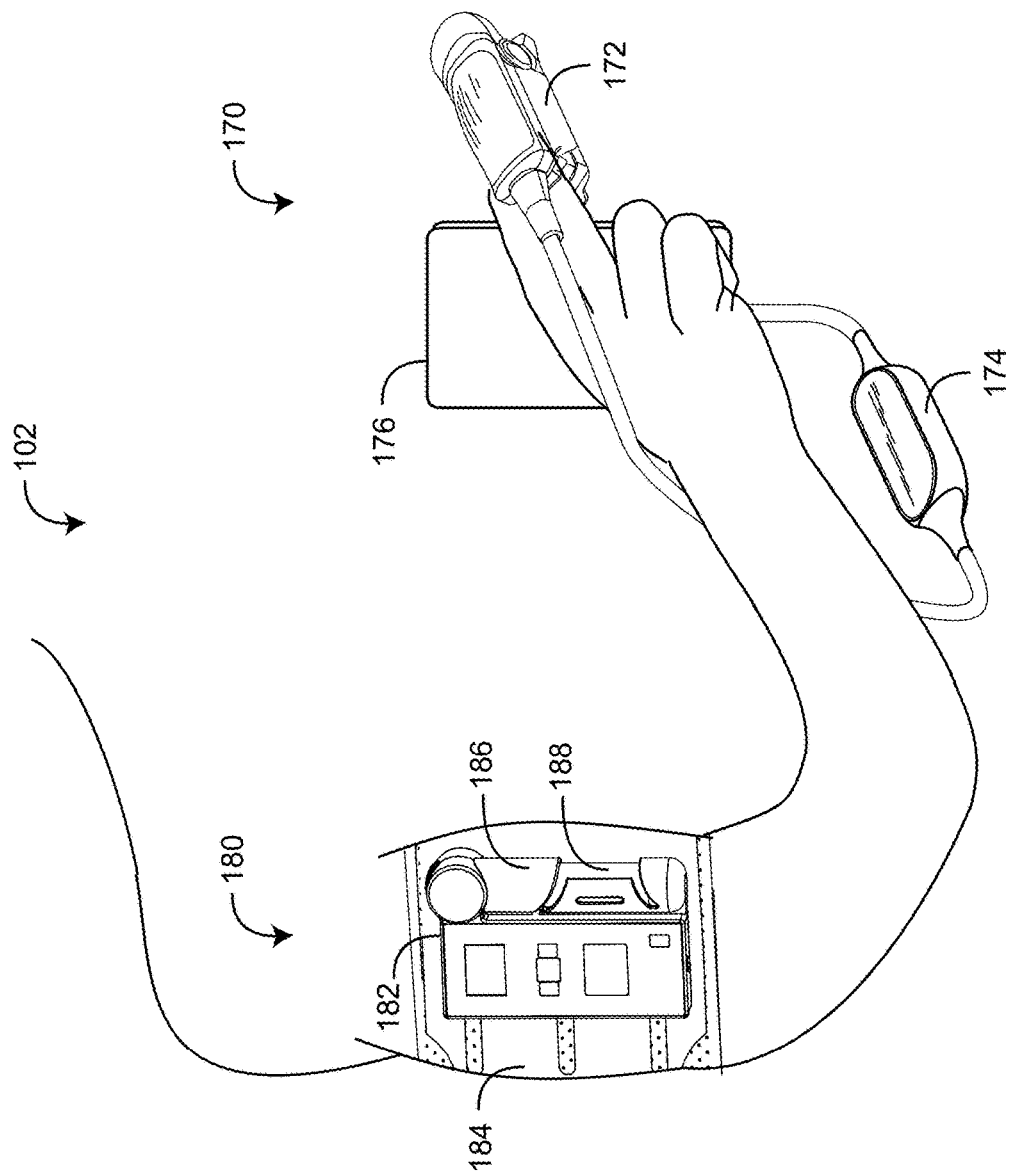

FIGS. 1A-B illustrate cloud-based physiological monitoring systems that are capable of blood parameter, blood pressure and other physiological measurements. As shown in FIG. 1A, a physiological monitoring system 101 advantageously provides spot check measurements of various blood constituents, such as blood glucose. The monitoring system 101 has a blood parameter monitor 130, an optical sensor 140, a sensor cable 150 electrically and mechanically interconnecting the monitor 130 and sensor 140 and a monitor-integrated test strip reader 160 that accepts test strips 165 via a test strip slot. In a particular use, the monitoring system 101 provides relatively frequent noninvasive measurements of blood glucose interspersed with relatively infrequent invasive measurements of blood glucose so as to manage individual blood glucose levels. The monitoring system 101 individually calibrates the sensor 140 measurements with intermittent test strip measurements to advantageously provide the accuracy of individualized glucose test strip measurements at a much-reduced frequency of blood draws. Reduced blood draws are a substantial aid to persons who require frequent monitoring of blood glucose levels to manage diabetes and related diseases. In an embodiment, the monitor 130 has a handheld-tablet housing including an integrated 5.6 in IPS touch screen 135 defining one or more input keys and providing a display of blood glucose levels among other features. The monitor 130 advantageously has Wi-Fi and 3G cellular communications for cabled and wireless cloud access. Cloud connectivity allows remote sensor data processing, algorithm development, individual blood glucose calibration and software updates among other cloud services. A blood parameter monitoring system is described with respect to U.S. patent application Ser. No. 13/646,659, filed Oct. 5, 2012, titled Noninvasive Blood Analysis System and U.S. patent application Ser. No. 13/726,539, filed Dec. 24, 2012, titled Blood Glucose Calibration System, both assigned to Cercacor and both incorporated in their entireties by reference herein.

As shown in FIG. 1B, a physiological monitoring system 102 may have two or more monitors 170, 180 in sensor communications with an individual person so as to generate multiple sensor data streams and display multiple types of physiological parameters. In an embodiment, the multiple monitors 102 include a handheld blood parameter monitor 170 and a arm cuff-mounted blood pressure monitor 180. In an embodiment, the handheld blood parameter monitor 170 has an optical sensor 172, a monitor module 174 and a handheld smart cellular telephone ("smart phone") 176. An optical sensor is described above with respect to FIG. 1A. The optical sensor attaches to a fleshy tissue site, such as a fingertip. The monitor module 174 drives LEDs in the optical sensor 172 and receives detector signals responsive to the LED emitted light after attenuation by the fleshy tissue and blood flow within the fleshy tissue. The blood flow may be active-pulsed and arterial-pulse blood flow. The monitor module 174 receives the detector signals, i.e. the raw sensor data stream and derives physiological parameters, which are communicated to the smart phone 176. This alleviates the smart phone 176 from the computationally-intense task of processing raw sensor data and deriving physiological parameters, which the current generation of smart phones are ill-equipped to perform. A combination optical sensor, monitor module and smart phone configured as a mobile physiological monitor are described in U.S. patent application Ser. No. 14/033,315, titled Physiological Monitor with Mobile Computing Device Connectivity, assigned to Cercacor and incorporated in its entirety by reference herein.

Also shown in FIG. 1B, in an embodiment, a cuff-mounted, blood pressure monitor 180 is attached to a person's limb so as to measure blood pressure parameters. The blood pressure monitor 180 has a monitor module 182, an inflatable cuff 184 and a gas chamber 186. The monitor module 182 is mounted to the inflatable cuff 184, is battery-operated and includes a display and a user interface. In an embodiment, the gas chamber 186 is configured for disposable $CO_2$ cartridges 188 in communications with a monitor-controlled gas valve for automatic cuff inflation. Also shown in FIG. 1B, the blood pressure monitor 180 has an OLED display, a 16 g $CO_2$ canister 188 for automatic cuff information, and Bluetooth and USB communication interfaces. Sensor capabilities include systolic and diastolic blood pressure parameters, pulse rate and mean arterial pressure (MAP). The blood pressure monitor 180 also has cloud communications capabilities either directly via a wireless wide area communications link or via local area communications (e.g. Wi-Fi, Bluetooth) with other devices that have such a wide area link, such as the smart phone 176. A cuff-mounted monitor is described in detail in U.S. patent application Ser. No. 13/838,225, filed Mar. 15, 2013, titled Patient Monitoring System, assigned to Cercacor and incorporated in its entirety by reference herein. These cloud-based physiological monitors 101-102 (FIGS. 1A-B) advantageously provide measurement capabilities for more than a dozen different noninvasive parameters in addition to cloud services including clinical data visualization, storage and exchange and real-time algorithm processing.

Further shown in FIG. 1B, a multiple-monitor configuration 102 can advantageously derive multiple sensor 170, 180 data streams and multiple physiological parameters from the same individual and communicate these data streams and parameters to the cloud, as described in further detail with respect to FIGS. 2-7, below. This advantageously allows a cloud-based processor to receive two or more independent sensor data streams, for example data from a blood pressure sensor and an optical sensor attached to an individual, and derive cross-sensor parameters such as the medical indices described below. Such cross-sensor parameters allow caregivers to assess a broader spectrum of physiological conditions from states and trends in these cross-sensor parameters than possible with a data stream from a single sensor.

Although a multiple-monitor configuration 102 is described above with respect to a blood pressure sensor and an optical sensor, each in communications with their individual monitors, in other embodiments, multiple sensors may be in communications with a single monitor. These sensors may include a variety of devices including accelerometers for data regarding body position and activity; body and environment temperature sensors; electrical sensors for deriving EEG, EKG data streams; acoustic sensors for detecting respiration and other body sounds; and capnography sensors for monitoring carbon dioxide, among others.

Additionally shown in FIG. 1B, in an embodiment, individual monitors 170, 180 may each communicate directly to the cloud utilizing wide area communications, such as wired or wireless Internet or cellular network devices. In an embodiment, a first monitor 170 may have wide area communications capability, and a second monitor 180 may use local area communications to communicate its sensor data to the first monitor 170 for transmission to a cloud-based processor. In another embodiment, first 170 and second 180 monitors may each use local area communications to communicate sensor data to a local processing device, such as a laptop or desktop computer that, in turn, uses wide area communications to communicate with a cloud-based processor. Various monitor-cloud data communications and processing scenarios are further described with respect to FIGS. 2-7, below.

Figure 2:
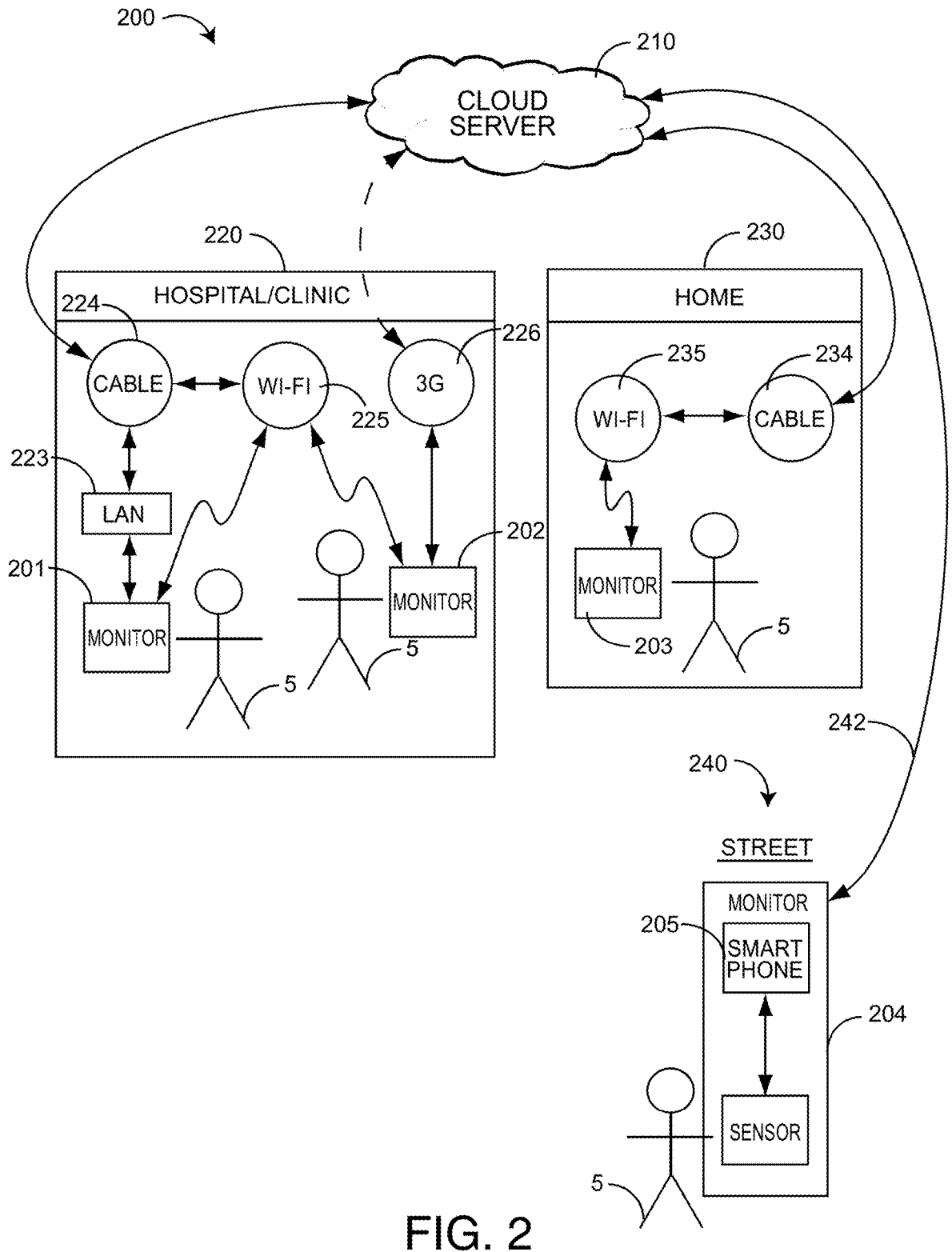
FIG. 2 is a general flow diagram of a cloud-based monitoring system.

FIG. 2 illustrates a cloud-based monitoring system 200 having a cloud server 210 in communications with physiological monitors 201-204, such as described with respect to FIGS. 1A-B, above. The monitors 201-204 are located in various hospital/clinic 220, home 230 and street 240 locations remote from the cloud server 210. In an embodiment, the cloud server 210 utilizes various sensor signal processing algorithms to estimate physiological parameters such as blood oxygen saturation, carboxyhemoglobin, methomoglobin, blood glucose, total hemoglobin and respiration rate, to name just a few. These parameters are derived from sensor data collected by the monitors 201-204 and transmitted to the cloud server 210 via various data transmission paths.

As shown in FIG. 2, data is transmitted from monitors 201-204 to the cloud server 210 via wired (e.g. LAN 223) or wireless (e.g. Wi-Fi 225) local networks to wide area media, such as Internet cable 224 or telecommunications (e.g. 3G 226) networks. Alternatively, a monitor 204 may have a wireless link 242 for direct data transmission to the cloud over a cellular network. These wide area media, in turn, are in communications with the cloud server 210, which calculates physiological parameters as described above. The calculated parameters are transmitted back to the monitors 201-204 or smart phone 205 for display, additional processing and storage of physiological parameters as well as corresponding notification and use by patients and their care providers.

Further shown in FIG. 2, the above-described configurations allow all monitors 201-204 to benefit from the same set of signal processing algorithms residing in the cloud server 210. At the same time, these signal processing algorithms can remain proprietary and protected from reverse engineering in the event any monitors 201-204 are lost or stolen, as the monitors 201-204 do not have access to the cloud algorithms. In particular, the monitors 201-204 only have access to raw (sensor) data, error messages and data pre-processing (e.g. for probe-off detection). In other embodiments, non-proprietary signal processing algorithms are resident in the monitors 201-204 and proprietary algorithms are resident in the cloud 210. In an embodiment, a dual communications channel between one or more monitors 201-204 and the cloud 210 may be implemented for redundancy, so as to resolve safety issues related to critical medical information and potential communication or monitor malfunctions. For example, a direct 3G (telecommunications) link between a monitor 201-204 and the cloud server 210 may be available as backup to landline communications.

Figure 3:
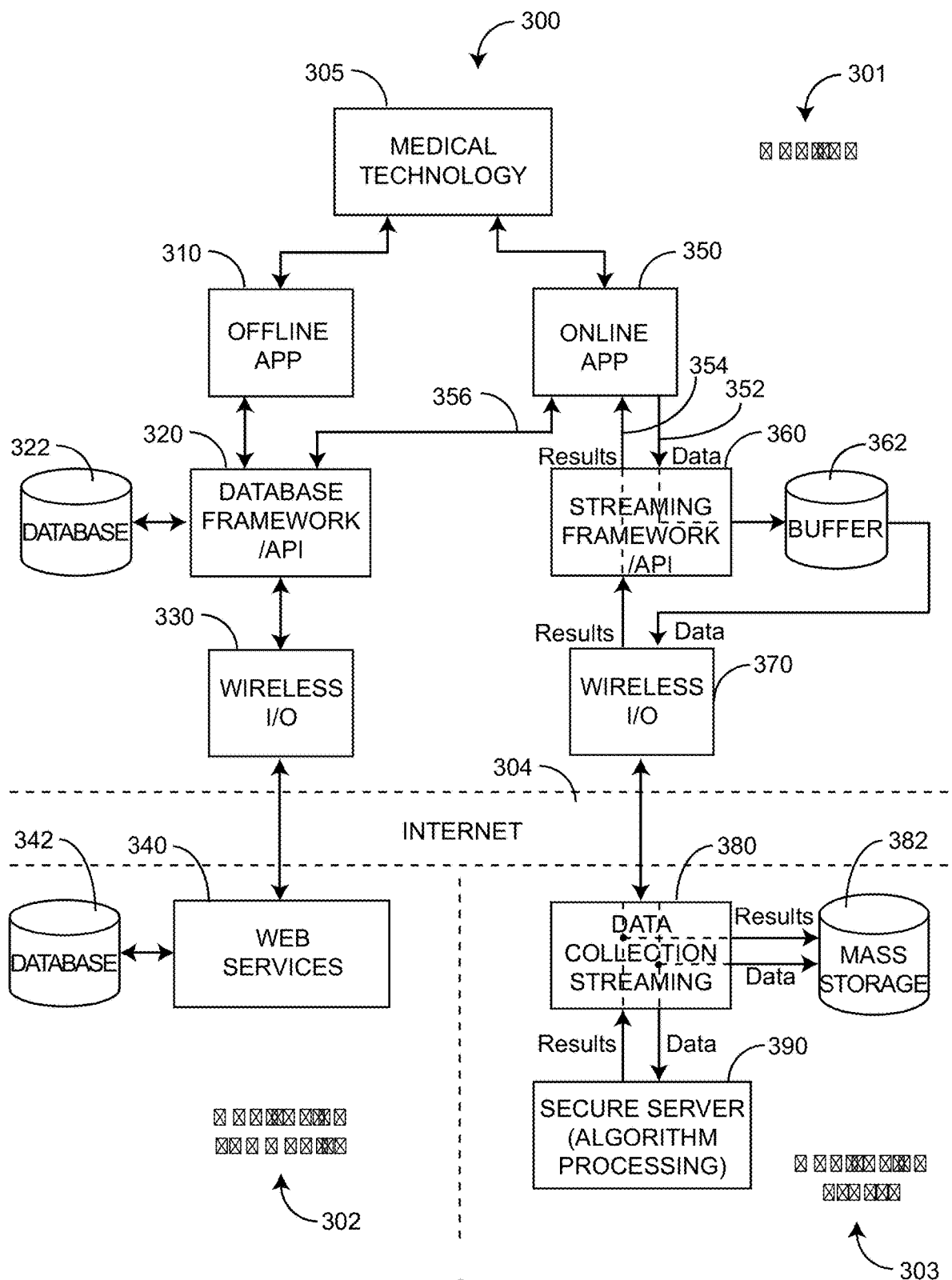
FIG. 3 is a detailed block diagram of a cloud-based monitoring system.

FIG. 3 illustrates a cloud-based physiological monitoring system 300 including a monitor 301, a monitoring community 302 and a monitoring center 303. A monitor 301 is in communications with one or more sensors, as described with respect to FIGS. 1A-B, above. In an embodiment, the monitor 301 includes medical technology 305 in addition to non-medical computer and telecommunication functions such as are available on any of various mobile consumer devices (not shown). Medical technology 305 includes both an offline application 310 and an online application 350 for measuring and managing blood glucose, blood pressure and other physiological parameters and medical indices.

As shown in FIG. 3, following successful calibration, the offline application 310 allows a patient to attach a sensor, e.g. 140 (FIG. 1A), push a monitor button, e.g. "Test," and initiate a sampling of sensor data and derivation of physiological parameters, such as blood glucose, utilizing resident processors and algorithms. The monitor 301 then displays the resulting physiological parameter value on a monitor display, e.g. 135 (FIG. 1A). The only "cloud" function the offline app 310 performs is to occasionally dump patient data, including derived physiological parameters and related information, from its database 322 to, say, a treating physician's database 342, so that the physician can monitor and review the patient's disease management and insure that the monitor and sensor are functioning normally. This feature also allows a patient to share their medical information with other members of the monitoring community 302, including family members or non-related persons having similar treatments and therapies, as described with respect to FIG. 5, below.

Also shown in FIG. 3, an online application 350 advantageously transmits the monitor 301 sensor data via the cloud (e.g. Internet 304) to the monitoring center 303, which is remote from the monitor 301 location. Physiological parameter processing algorithms reside in a secure server 390, which derives blood glucose values, other blood constituent values and measurements of other physiological parameters, such as blood pressure, with very small latency times. A data buffer 362 in the monitor 301 reduces transmit data latency times. The calculated physiological parameter results are immediately returned to the monitor 301 for display.

Further shown in FIG. 3, the monitoring center 303, which is accessed via the online application 350, has more processing power and is easier to maintain than the offline application 310. In particular, algorithm 390 modifications and upgrades can be made simply and quickly at the monitoring center 303 site as compared to upgrades across many monitors 301 distributed over disparate locations. Further, the monitoring center 303 processors have significantly greater computational capabilities than the relatively limited processors residing in each monitor 301. Also, algorithms developed at the monitor manufacturer's facility typically have to be reduced in size and ported to a different programming language for installation in each monitor 301, which requires speed and memory size tradeoffs that are nonexistent at the monitoring center 303. In addition, the processor intensive computations required for offline applications raise heat dissipation issues for relatively compact handheld and tablet monitors. The downside of the monitoring center 303 is the necessity of reliable connectivity to all of the monitors 301.

According to the trade-offs described above, in a particularly advantageous embodiment, the online application 350 is utilized for cloud computing of all physiological parameters or at least the most computationally intense parameters unless cloud access is temporarily unavailable. In the event the monitoring center 303 processors are down or the online application 350 communications link with the monitoring center 303 is lost, then the offline application 310 performs the necessary computations. This can be done in an emergency for a few minutes without concern about monitor 301 heat dissipation limitations. Further, for blood glucose measurements, loss of cloud access is mitigated somewhat by the device strip reader 160 (FIG. 1A), which is always available to users in the event the monitoring center 303 is "down" or when a particular monitor 301 has no cloud access.

In a particularly advantageous blood glucose management embodiment, the offline application 310 has a setting for the maximum time allowed between invasive (test strip) measurements of blood glucose. The offline application 310 tracks the time that has elapsed since the last test strip measurement was made and disables noninvasive blood glucose monitoring if that elapsed time limit is exceeded. In an embodiment, the offline application 310 provides a user one or more warning messages of an impending noninvasive measurement timeout due to an excessive elapsed time from the last invasive measurement. In an embodiment, either the offline application 350 or the online application 310 may adjust the maximum time allowed between invasive measurements as a function of the delta time and the delta blood glucose values between two consecutive invasive measurements. This maximum elapsed time adjustment advantageously takes into account relatively small changes, historically, in invasive glucose values over relatively long time spans so as to lengthen the maximum-allowed elapsed time between invasive measurements. Likewise, the maximum elapsed time adjustment takes into account relatively large changes, historically, in invasive glucose values over relatively short time spans so as to shorten the maximum-allowed elapsed time between invasive measurements.

Figures 4A, 4B:
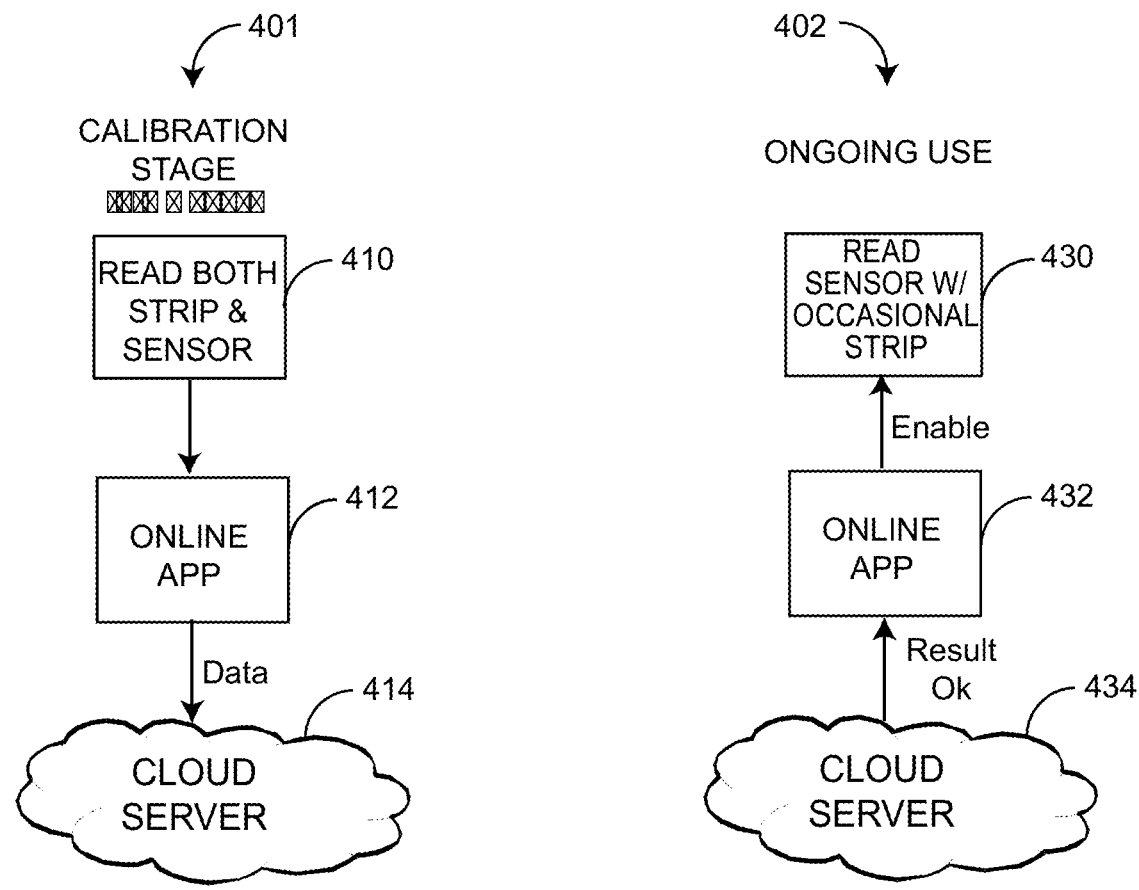
FIGS. 4A-B are general flow diagrams of blood glucose calibration.

FIGS. 4A-B illustrate a blood parameter calibration process 401-402 that includes set-up and calibration functions for a cloud-based physiological monitor, such as described with respect to FIGS. 1-3, above. FIG. 4A illustrates an initial calibration stage 401 when a new user attempts to calibrate their monitoring system, e.g. 101 (FIG. 1A) using a strip reader 160 and test strip 165 (FIG. 1A). At regular intervals, blood samples are read with a strip at the same time that optical sensor 140 (FIG. 11) data is taken 410. An online application 412 sends the strip and sensor data to a cloud server 414. See, e.g., 303, 350 (FIG. 3). The strip readings are then compared to calculations based upon optical sensor 140 (FIG. 1A) measurements. If there are consistent matches between the invasive and noninvasive measurements, the calibration stage 401 is complete. If not, the calibration stage 401 continues. This process may take 1 to 6 weeks and, in some cases, may not be successful. That is, after some predetermined number of measurements or calibration time interval, the strip readings may not correlate with the optical sensor-based measurements. As a result, that particular individual is deemed not suitable for noninvasive glucose monitoring. FIG. 4B illustrates an ongoing use 402 once the user is initially calibrated 401. The cloud server 434 indicates to the online application 432 that the user is calibrated 401. The monitoring system 101 (FIG. 1A) is enabled accordingly 430 to use sensor-based measurements with occasional strip measurements to insure up-to-date calibration. This calibration process 401, 402 is particularly advantageous with respect to calibrating a cloud-based physiological monitor for noninvasive (optical sensor) blood glucose measurements interleaved with occasional invasive (glucose test strip) measurements.

Figure 5:
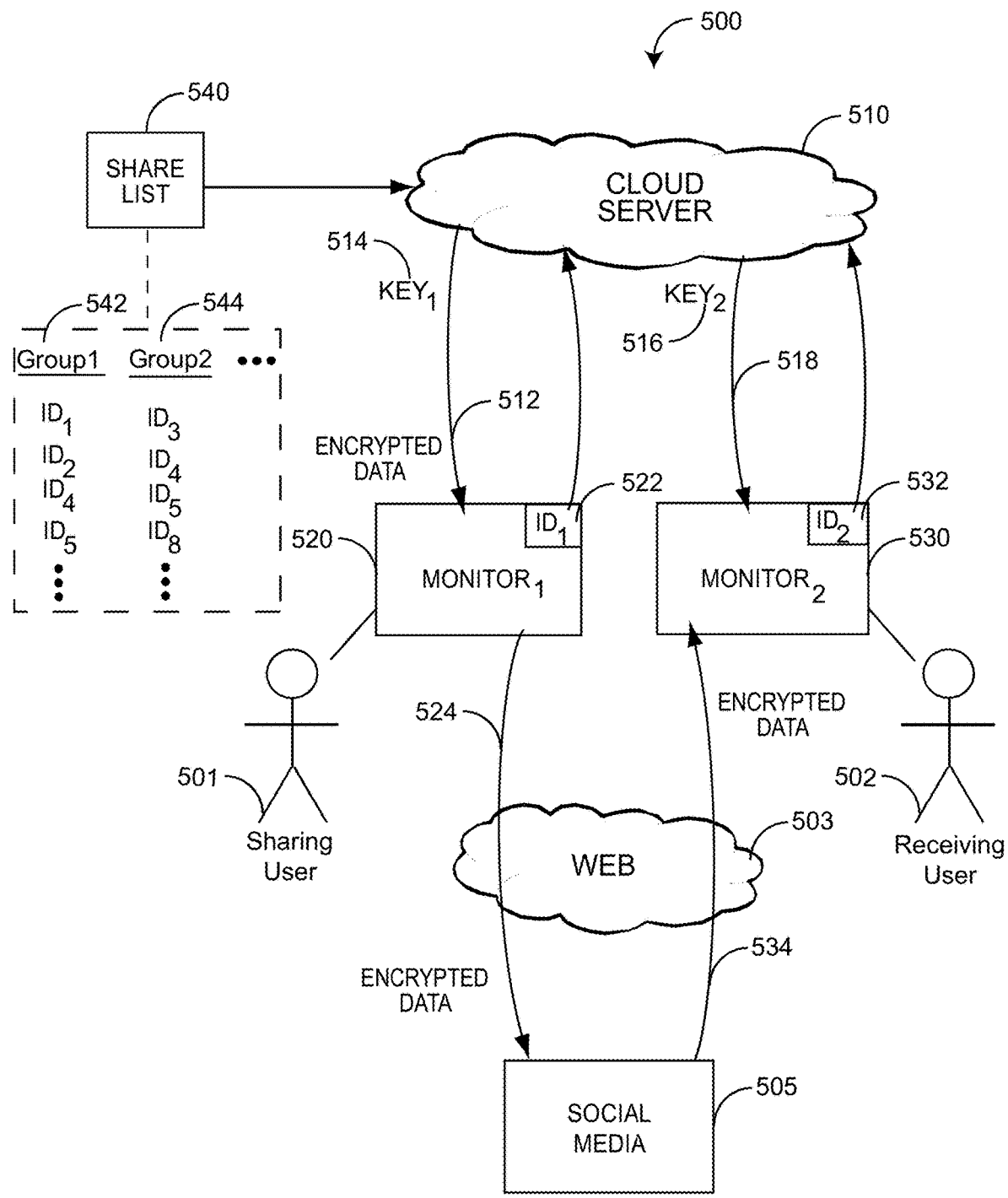
FIG. 5 is a general flow diagram of a cloud-based, protected social network for sharing monitoring measurements.

FIG. 5 illustrates a cloud-based, secure social network 500 that enables a monitor 101-102 (FIGS. 1A-B) user to confidentially share their medical information with a trusted group of other users. Medical information may include measured physiological parameters and a user's health management experiences. For example, medical information may be a past history of blood glucose measurements; steps taken to control blood glucose, including medication, diet and exercise; and recent blood glucose measurement results. The social media 505 for sharing this medical information may be any of the popular social media sites, such as Facebook or Google+, to name a few. The protected social network 500 incorporates cloud-based monitors 520, 530 in communications with a cloud server 510, as described with respect to FIGS. 1-4, above.

As shown in FIG. 5, each sharing user 501 communicates with the cloud server 510 so as to establish a share list 540 of one or more groups 542, 544 of receiving users 502 who are allowed to view the sharing user's medical information. Receiving user groups 542, 544 may be based upon, or restricted by, the type and scope of medical information shared. Each user 501, 502 is advantageously identified according to their monitor device ID 522, 532, which is securely registered with the cloud server 510. That is, one advantage of a cloud-based secure social network 500 is that only individuals assigned a monitor 520, 530 can belong, and membership in and use of the protected social network 500 is enforced by the cloud server 510 and its recognition of monitor IDs 522, 532. Accordingly, a sharing user's share list 540 securely establishes monitors 530 that receive monitoring data and other personal information regarding the sharing user 501.

Also shown in FIG. 5, the cloud server 510 advantageously manages encryption of share data according to the sharing user 501 and their share list 540. The cloud server 510 collects and stores monitoring device 520 data and calculates and stores corresponding measurement results, which may include share data. The cloud server 510 encrypts share data 512, which is transmitted from the cloud to the sharing user's monitor 520. A corresponding $KEY_1$ 514 based upon the sharing user's monitoring device $ID_1$ 522 is also transmitted to the sharing user's device 520. This allows the sharing user 501 to decrypt and view share data. A separate $KEY_2$ 516 is transmitted to a monitor 530 corresponding to a receiving user 502 listed on the share list 542. The cloud server 510 generates $KEY_2$ 516 according to the receiving user's device $ID_2$ 532.

Further shown in FIG. 5, the sharing user 501 can post the encrypted share data 524, at their discretion, to social media 505 of their choosing. A receiving user 502, at their discretion, can upload the encrypted data 534 and use their device specific $KEY_2$ 516 to decrypt and view the share data. Advantageously, the cloud server 510 in this secure data sharing architecture does not require a customized data sharing website and the corresponding setup and site management burdens. Cloud server 510 overhead is limited to share list 540 management, data encryption and key generation and encrypted data and key distribution based upon an existing network of monitors 520, 530 with registered and readable device IDs 522, 532.

Figure 6:
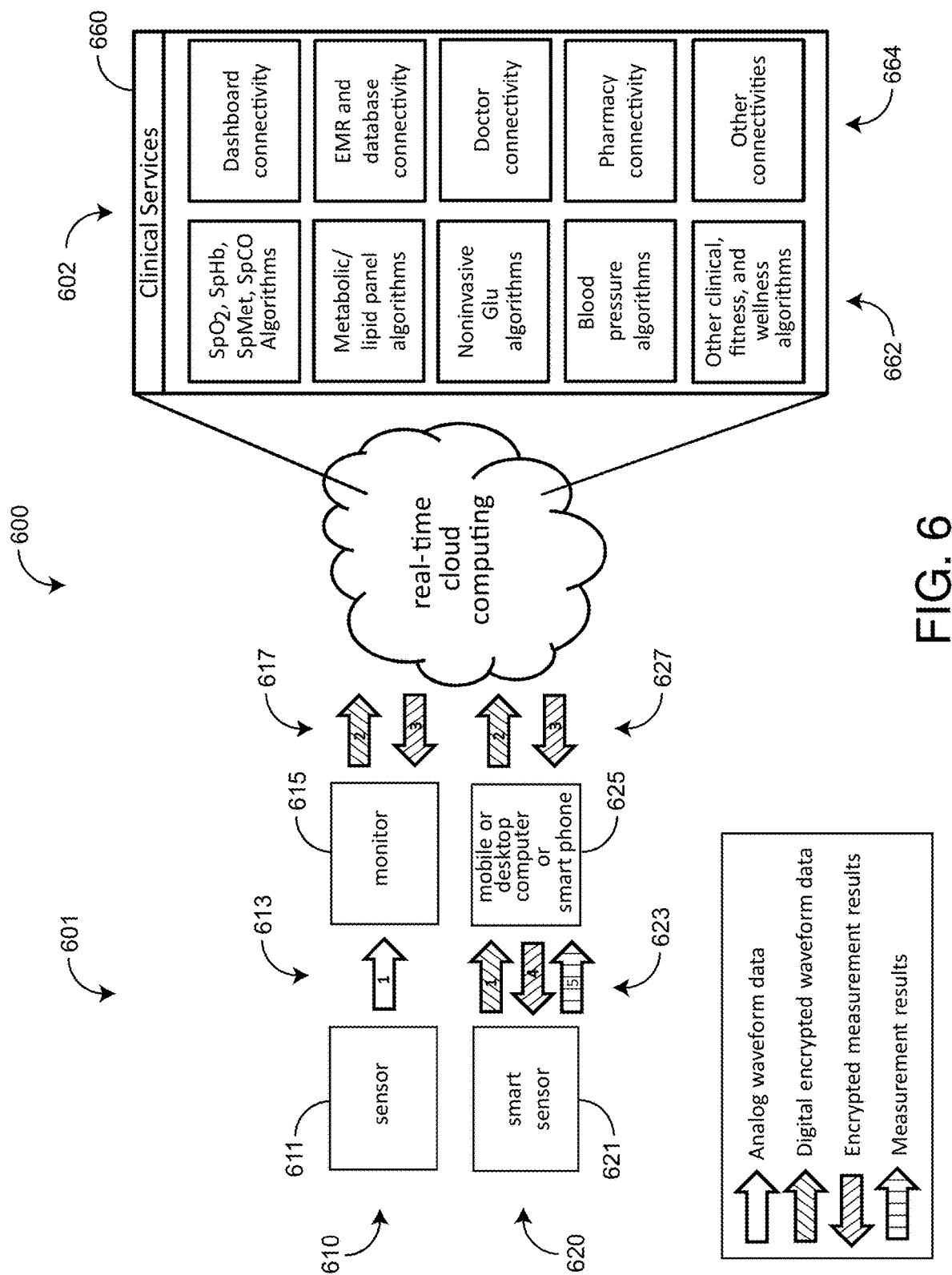
FIG. 6 is a general flow diagram of real-time algorithm processing using one or more of a sensor and connected medical device or a smart sensor and connected mobile or desktop device in communications with a cloud service so as to perform clinical services including physiological parameter calculations.

FIG. 6 illustrates a real-time cloud computing architecture 600. On a user side 601, various physiological monitoring systems 610, 620 exist in perhaps widespread geographical locations and disparate environments. In contrast, a centralized cloud server 602 provides a variety of clinical services 660 for these monitoring systems 610, 620. In an embodiment, various users each possess a physiological monitoring system 610 having a sensor 611 and a corresponding monitor 615, such as described with respect to FIG. 1A, above. The sensor 611 generates an analog data stream 613 responsive to at least some aspect of the user's physiology. The monitor 615 receives and processes the analog data stream 613 and generates an digital encrypted data stream 617 responsive to the sensor 611. For example, the data stream 617 may be optical sensor data that has been filtered, digitized, amplified, demodulated and decimated in the monitor 615 and then encrypted and transmitted to the cloud server 602.

As shown in FIG. 6, in an embodiment, various other users each possess a physiological monitoring system 620 having a smart sensor 621 and a corresponding smart phone 625, such as described with respect to FIG. 1B, above. (A mobile or desktop computer 625 may be used in lieu of a smart phone). The smart sensor 621 generates an analog data stream 613 responsive to at least some aspect of a user's physiology. A monitor module integral to the smart sensor 621 receives and processes the analog data stream and generates a digital encrypted data stream 623 responsive to the analog data stream. The smart phone 625 receives the digital encrypted data stream 623 and transmits it directly to the cloud server 602.

Also shown in FIG. 6, clinical services performed in the cloud 602 include algorithm computations 662 and connectivity 664. Algorithms 662 include those for calculating $SpO_2$, SpHb, SpMet and SpCO; metabolic and lipid parameters; noninvasive blood glucose parameters; blood pressure parameters and other clinical, fitness and wellness-related parameters. Connectivity 664 includes dashboard, EMR and database, doctor and pharmacy connectivities. The cloud 602 returns encrypted measurement results 627 to the monitor 615 or the smart phone 625. The smart phone 625 passes the encrypted measurement results 623 to the smart sensor 621, and the smart sensor 621 sends the (decrypted) measurement results 623 back to the smart phone 625.

The advantages of real-time medical parameter computing via the cloud 602 is flexibility, scalability and ease of maintenance of the algorithm portfolio. In addition, the cloud offers significant IP protection for these algorithms because algorithms are not calculated within a device exposed to hands-on reverse engineering. The disadvantages are that medical parameter cloud computing requires highly reliable connectivity combined with patient risk mitigation if such connectivity is lost.

Figure 7:
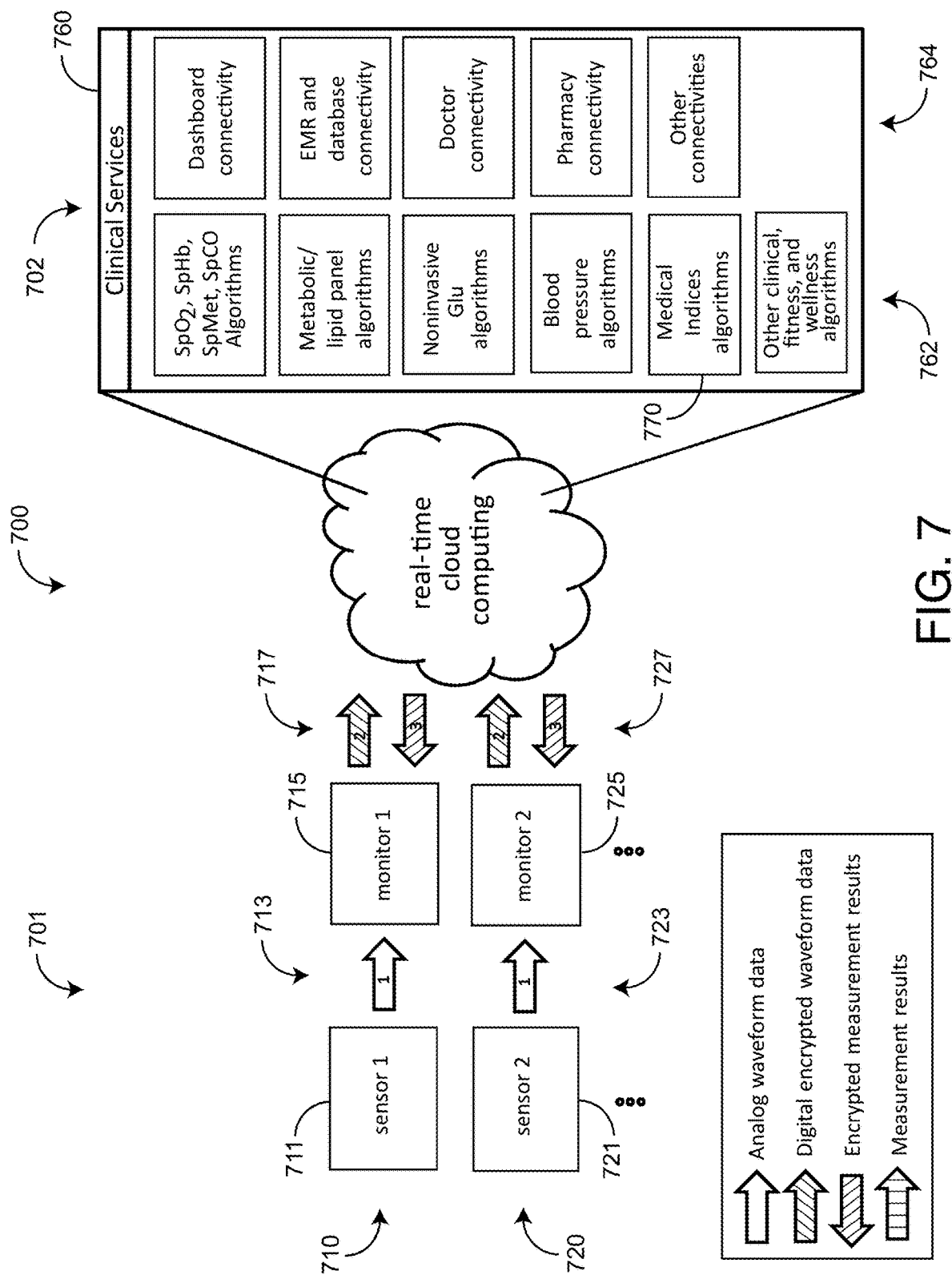
FIG. 7 is a general flow diagram of real-time algorithm processing using multiple sensors and connected medical devices in communications with a cloud service so as to perform clinical services including calculations of medical indices.

FIG. 7 illustrates another real-time cloud-computing architecture 700. In particular, multiple sensors 711, 721 in conjunction with corresponding monitors 715, 725, such as described with respect to FIGS. 1A-B, above, provide clinical services 760 via real-time cloud computing. Clinical services 760 performed in the cloud include the calculation of one or more blood constituents and blood pressure. Blood constituent calculations include oxygen saturation, normal and abnormal hemoglobin, metabolic and lipid constituents and glucose, as described with respect to FIG. 6, above. Also as described with respect to FIG. 6, above, data flow for a sensor 711, 721 and connected monitor 715, 725 includes analog waveform data from the sensor 711, 721 to the connected monitor 715, 725; digital encrypted waveform data to the cloud 717,727, which returns encrypted measurement results 717,727 to the monitor 715, 725.

As shown in FIG. 7, clinical services 760 further include calculation of medical indices 770, each of which are combinations of physiological parameters. As such, two or more monitors 715, 725 independently generate encrypted waveform data 717, 727 used to derive a medical index 770. The cloud 760 time synchronizes this data accordingly. In an embodiment, each device has a master clock so as to record a universal time. The cloud server 702 corrects for time differences and delays among devices that are part of the same user account. As an example, a user acquires a smart sensor/smart phone 170 (FIG. 1B) and a cuff-based blood pressure monitor 180 (FIG. 1B). The user registers these devices via their cloud account. After that, when measurements are taken, the cloud server 702 verifies if the set of required parameters are available for a particular medical index 770 and if the parameters were measured within the required time frame for these parameters.

As an example, blood pressure constantly varies. Therefore, when calculating an index involving other parameters, any measurement time frame mismatch should be small (a few minutes). In contrast, total cholesterol changes very slowly, and therefore the measurement time frame mismatch with respect to other parameters can be much larger (hours). If any time frame mismatch between measured parameters for a particular medical index is within tolerance, the cloud server 702 processes and displays the index on at least one of the user's monitors 715, 725. If a time frame mismatch is too large, then each of the monitor 715, 725 displays are dashed out for that index.

FIGS. 8A-F illustrate medical indices 800 based upon trends in some or all of selected blood constituents, e.g. Hgb (hemoglobin), BUN (blood urea nitrogen) and Cr (creatinine); plethysmograph waveform features, e.g. plethysmograph variability index (PVI) and blood pressure (BP) that are indicative of dehydration 810, renal insufficiency 820, over-hydration 830, gastrointestinal bleeding 840, congestive heart failure exacerbation 850 and cardiovascular risk 860, respectively. Specifically, if a monitor and sensor are only capable of, or enabled to, measure blood constituent parameters, then a particular medical index ("index") may be based exclusively upon, say, Hgb, BUN and Cr. If a monitor and sensor are also capable of, or enabled to, measure plethysmograph waveform features, then that index may be based upon Hgb, BUN, Cr and PVI. (See, e.g. FIG. 1A). Further, if one or more monitors/sensors attach to a person, then that index may be based upon Hgb, BUN, Cr, PVI and BP. (See, e.g. FIG. 1B). A plethysmograph variability index (PVI) is described with respect to U.S. Pat. No. 8,414,499, filed Dec. 7, 2007, titled "Plethysmograph Variability Processor" assigned to Masimo and incorporated in its entirety by reference herein. Note that PVI is not to be confused herein with a medical index although PVI may be used to calculate or otherwise indicate one or more medical indices.

As described herein, a medical index 800 is an indicator of the physiological status of a living being. Physiological status may be a positive condition, such as strength, endurance or conditioning, or a negative condition, such as a disease state or physiological weakness, to name a few examples. In an embodiment, a medical index ("index") has a binary value. That is, the index indicates a likelihood of the existence or nonexistence of a particular physiological status such as dehydration 810, renal insufficiency 820, over-hydration 830, gastrointestinal bleeding 840, CHF exacerbation 850 and cardiovascular risk 860, to name a few. In other embodiments, a medical index has a set of discrete values, such as a scale from 1 to 10. For example, 1 may indicate a very low likelihood and 10 a very high likelihood of a particular physiological status. In yet another embodiment, a medical index may have a continuous range of values, such as 0-100% so as to represent, for example, a probability that a particular medical condition exists.

Figures 8A, 8B, 8C:
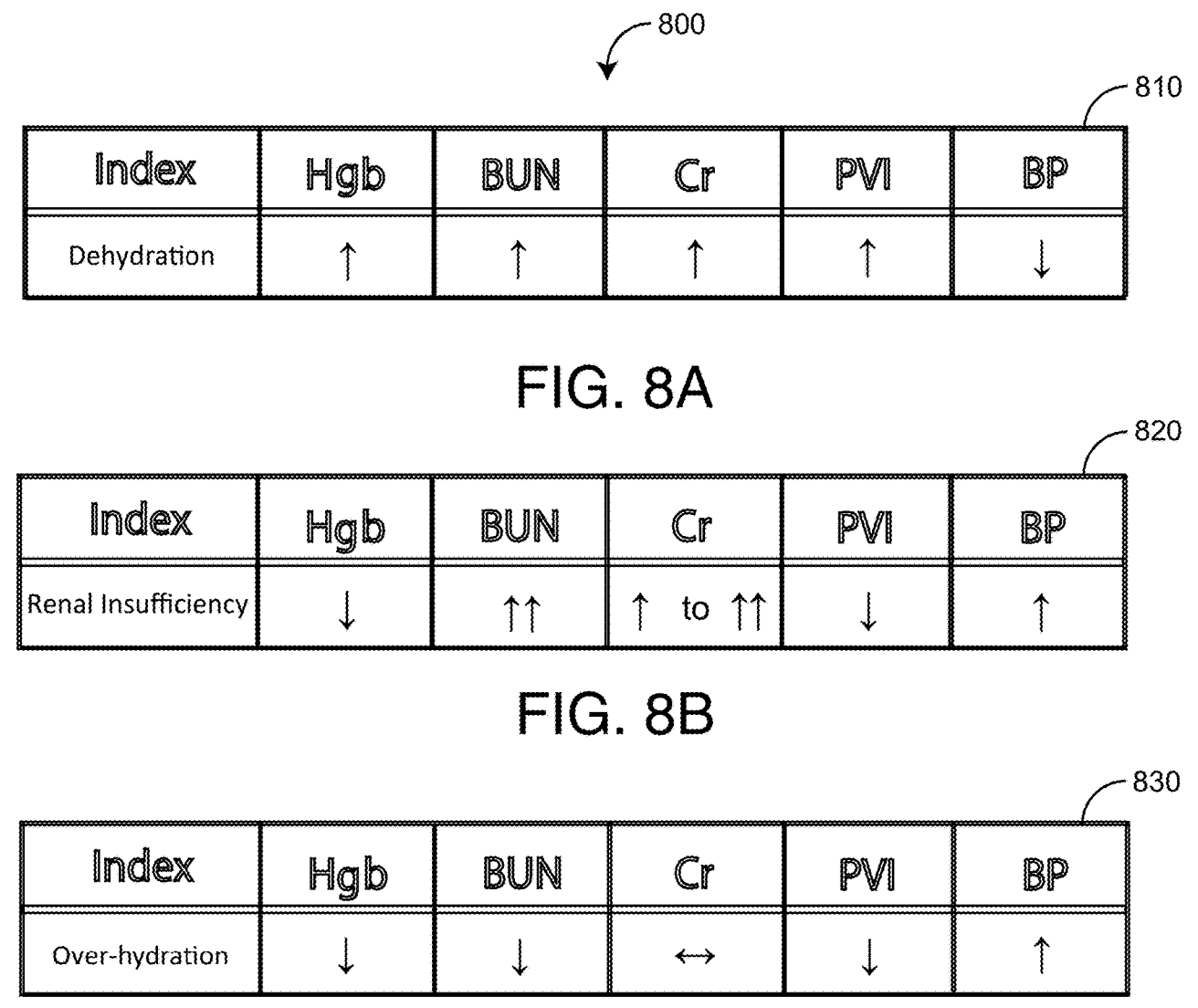

As shown in FIG. 8A, dehydration 810 may be indicated from noninvasive measurements of Hgb, BUN and Cr, and in particular from rising values for each of these constituents over a predetermined time interval "$\Delta t_{dh}$." If available, rising values of PVI over $\Delta t_{dh}$ further indicate dehydration. If available, falling values of BP over $\Delta t_{dh}$ further indicate dehydration.

As shown in FIG. 8B, renal insufficiency 820 may be indicated from noninvasive measurements of Hgb, BUN and Cr, and in particular from falling values of Hgb, relatively fast rising values of BUN and rising to relatively fast rising values of Cr over a predetermined time interval "$\Delta t_{ri}$." If available, falling values of PVI over $\Delta t_{ri}$ further indicate renal insufficiency. If available, falling values of BP over $\Delta t_{ri}$ further indicate renal insufficiency.

As shown in FIG. 8C, over-hydration 830 may be indicated from noninvasive measurements of Hgb, BUN and Cr, and in particular from falling values of Hgb and BUN over a predetermined time interval "$\Delta t_{oh}$" and relatively constant values of Cr over $\Delta t_{oh}$. If available, falling values of PVI over $\Delta t_{oh}$ further indicate over-hydration. If available, rising values of BP over $\Delta t_{oh}$ further indicate over-hydration.

As shown in FIG. 8D, gastrointestinal bleeding 840 may be indicated from noninvasive measurements of Hgb, BUN and Cr, and in particular from falling levels Hgb over a predetermined time interval "$\Delta t_{gi}$." If available, rising values of PVI over $\Delta t_{gi}$ further indicate gastrointestinal bleeding. If available, falling values of BP over $\Delta t_{gi}$ further indicate gastrointestinal bleeding.

As shown in FIG. 8E, CHF exacerbation 850 may be indicated from noninvasive measurements of Hgb, BUN and Cr, and in particular from stable to falling levels of Hgb and BUN and stable to rising levels of Cr over a predetermined time interval "$\Delta t_{chf}$." If available, falling values of PVI over $\Delta t_{chf}$ further indicate CHF exacerbation. If available, relatively constant or rising values of BP over $\Delta t_{chf}$ further indicate CHF exacerbation.

As shown in FIG. 8F, cardiovascular risk 860 may be indicated from noninvasive measurements of Chol, HDL, Chol/HDL and Trig and in particular from rising levels of Chol, Chol/HDL and Trig and falling levels of HDL over a predetermined time interval "$\Delta t_{cvr}$." If available, rising values of BP over "$\Delta t_{cvr}$" further indicate cardiovascular risk.

In an embodiment $\Delta t_{xx}$ are the same for each index, i.e. $\Delta t_{dh} = \Delta t_{ri} = \Delta t_{oh} = \Delta t_{gi} = \Delta t_{chf} = \Delta t_{cv}$. In an embodiment, $\Delta t_{xx}$ varies for each constituent of a particular index, e.g. $\Delta t_{xx}(\text{Hgb}) \neq \Delta t_{xx}(\text{BUN}) \neq \Delta t_{xx}(\text{Cr}) \neq \Delta t_{xx}(\text{PVI}) \neq \Delta t_{xx}(\text{BP})$. The order of the particular constituents for each index is not intended to indicate the relative weight of that constituent for determining a particular index. For example, the listing of Hgb first in tables 8A-E does not suggest Hgb is more indicative of determining a particular index than BUN, Cr, PVI or BP. In an embodiment, indices are calculated over a fixed $\Delta t$ for one or more constituents. In an embodiment, indices are a function of a delta parameter value over a fixed $\Delta t$, e.g. $\Delta \text{BUN}/\Delta t$.

FIG. 9 illustrates trends in various physiological parameters, including blood-constituents, oxygen saturation, blood pressure, respiration rate (RR), temperature and heart-related parameters including heart rate (HR) and electrocardiogram (ECG) waveform features indicative of various physiological conditions, maladies and diseases. The use of one or more of these physiological parameters for determining a particular medical index depends on the availability of sensors, processors and algorithms for measuring these physiological parameters. Further, as noted above, the order of listing of various parameters in this table is not intended to indicate the relative sensitivity of a particular index to these parameters or the relative accuracy of determining a particular index utilizing these parameters.

Medical indices are described with respect to FIGS. 8-9, above, as based upon trends in various physiological parameters, i.e. changes in physiological parameters over time. This advantageously reduces the effect of individual variations in the baseline values for these physiological parameters, especially when the "normal" range for a particular physiological parameter is relatively broad. In other embodiments, however, medical indices may be based upon physiological parameter values in lieu of or in addition to physiological parameter trends, which advantageously allows a spot-check medical index calculation. As such, the up, sideways, and down arrows of FIGS. 8-9 can represent high (or very high), normal, and low (or very low) physiological parameter values so as to indicate a particular index.

In other embodiments, medical indices may be based upon fitness parameters derived, in part, from activity and location sensors, such as accelerometers and GPS devices, so as to measure, as examples, distance walked, calories burned, activity duration and intensity. These measurements may be combined with one or more of the parameters listed in FIG. 9 so as to derive medical indices indicative of exercise tolerance, cardiac function and arrhythmia analysis, to name a few.

A cloud-based physiological monitoring system has been disclosed in detail in connection with various embodiments. These embodiments are disclosed by way of examples only and are not to limit the scope of this disclosure or any claims that follow. One of ordinary skill in art will appreciate many variations and modifications.

What is claimed is:

1. A physiological monitoring system comprising:
   an optical sensor configured to provide a first data stream responsive to at least one of: pulsatile blood flow of a patient, or a blood constituent parameter of the patient;
   a blood pressure sensor configured to provide a second data stream responsive to blood pressure of the patient;
   one or more patient monitors configured to receive at least the first and second data streams; and
   one or more processors separate from the one or more patient monitors and configured to communicate with the one or more patient monitors and execute program instructions to cause the one or more processors to:
   communicate with the one or more patient monitors to receive information responsive to at least the first and second data streams and responsive to changes in one or more physiological conditions of the patient;
   process the information so as to derive a plurality of parameters responsive to the changes in the one or more physiological conditions of the patient;
   determine a plurality of trends in each of the plurality of parameters, wherein determining the plurality of trends includes:
   identifying, based on a type of a first parameter of the plurality of parameters, a first predetermined time interval that is specific to the first parameter;
   identifying, based on a type of a second parameter of the plurality of parameters, a second predetermined time interval that is specific to the second parameter and that is different from the first predetermined time interval;
   determining a trend of the first parameter over the first predetermined time interval, wherein the trend of the first parameter indicates either rising values of the first parameter over the first predetermined time interval or falling values of the first parameter over the first predetermined time interval; and
   determining a trend of the second parameter over the second predetermined time interval, wherein the trend of the second parameter indicates either rising values of the second parameter over the second predetermined time interval or falling values of the second parameter over the second predetermined time interval;
   combine the plurality of determined trends, including the trend of the first parameter over the first predetermined time interval, and further including the trend of the second parameter over the second predetermined time interval that is different from the first predetermined time interval, to derive a medical index, the medical index indicating a medical condition of the patient; and communicate the medical index to at least one of the one or more patient monitors,
wherein the one or more patient monitors are configured to:
    determine whether communication with the one or more processors is available or not available;
    responsive to determining that communication with the one or more processors is not available, temporarily process at least the first and second data streams locally at the one or more patient monitors; and
    responsive to determining that communication with the one or more processors is available, communicate the information responsive to at least the first and second data streams to the one or more processors.

2. The physiological monitoring system according to claim 1, wherein the one or more processors are configured to execute the program instructions to further cause the one or more processors to:
    cause display of the medical index on at least one of: the at least one of the patient monitors, or a smart cellular telephone.

3. The physiological monitoring system according to claim 2, wherein the medical index relates to at least one of: dehydration, renal insufficiency, over hydration, gastrointestinal bleeding, congestive heart failure exacerbation, or cardiovascular risk.

4. The physiological monitoring system according to claim 3, wherein the one or more processors are configured to execute the program instructions to further cause the one or more processors to:
    determine that required parameters for deriving the medical index include the plurality of parameters, and that the plurality of parameters are available for deriving the medical index; and
    determine that most-recent parameter measurements associated with the plurality of parameters satisfy a time frame mismatch tolerance associated with the medical index.

5. The physiological monitoring system according to claim 4, wherein determining the trends and deriving the medical index are performed in response to determining that most-recent parameter measurements associated with the plurality of parameters satisfy the time frame mismatch tolerance associated with the medical index.

6. The physiological monitoring system according to claim 5, wherein the one or more processors are configured to execute the program instructions to further cause the one or more processors to:
    in response to determining that the most-recent parameter measurements associated with the plurality of parameters do not satisfy the time frame mismatch tolerance:
        not derive the medical index; and
        cause the at least one of the patient monitor or the smart cellular telephone to not display the medical index.

7. The physiological monitoring system according to claim 6, wherein causing the at least one of the patient monitor or the smart cellular telephone to not display the medical index further includes displaying dashes in a location on the at least one of the patient monitor or the smart cellular telephone where the medical index otherwise would be displayed.

8. The physiological monitoring system according to claim 1, wherein the plurality of parameters include:
    a first parameter indicative of hemoglobin (Hgb) of the patient,
    a second parameter indicative of blood urea nitrogen (BUN) of the patient,
    a third parameter indicative of creatinine (Cr) of the patient,
    a fourth parameter indicative of a plethysmograph variability index (PVI) of the patient, and
    a fifth parameter indicative of a blood pressure (BP) of the patient.

9. The physiological monitoring system according to claim 1, wherein the plurality of parameters include:
    a first parameter indicative of total cholesterol (Chol) of the patient,
    a second parameter indicative of high-density lipoprotein (HDL) of the patient,
    a third parameter indicative of Chol/HDL of the patient,
    a fourth parameter indicative of triglycerides (Trig) of the patient, and
    a fifth parameter indicative of a blood pressure (BP) of the patient.

10. The physiological monitoring system according to claim 1, wherein the plurality of parameters include at least one of: hemoglobin (Hgb), blood urea nitrogen (BUN), creatinine (Cr), plethysmograph variability index (PVI), blood pressure (BP), total cholesterol (Chol), high-density lipoprotein (HDL), Chol/HDL, triglycerides (Trig), blood-constituents, oxygen saturation ($SpO_2$), respiration rate (RR), temperature, heart rate (HR), or electrocardiogram (ECG).

11. A physiological monitoring method comprising:
    receiving, from an optical sensor in communication with a patient and via a patient monitor, first sensor data responsive to at least one of: pulsatile blood flow of the patient, or a blood constituent parameter of the patient;
    receiving, from a blood pressure sensor in communication with the patient and via the patient monitor, second sensor data responsive to blood pressure of the patient;
    by one or more processors, separate from the patient monitor, executing program instructions:
        communicating with the patient monitor to receive at least the first and second sensor data responsive to changes in one or more physiological conditions of the patient;
        processing at least the first and second sensor data so as to derive a plurality of parameters responsive to the changes in the one or more physiological conditions of the patient;
        determining a plurality of trends in each of the plurality of parameters, wherein determining the plurality of trends includes:
            identifying, based on a type of a first parameter of the plurality of parameters, a first predetermined time interval that is specific to the first parameter;
            identifying, based on a type of a second parameter of the plurality of parameters, a second predetermined time interval that is specific to the second first parameter and that is different from the first predetermined time interval;
            determining a trend of the first parameter over the first predetermined time interval, wherein the trend of the first parameter indicates either rising values of the first parameter over the first predetermined time interval or falling values of the first parameter over the first predetermined time interval; and
            determining a trend of the second parameter over the second predetermined time interval, wherein the trend of the second parameter indicates either rising values of the second parameter over the second predetermined time interval or falling values of the second parameter over the second predetermined time interval;

combining the plurality of determined trends, including the trend of the first parameter over the first predetermined time interval, and further including the trend of the second parameter over the second predetermined time interval that is different from the first predetermined time interval, to derive a medical index, the medical index indicating a medical condition of the patient; and communicating the medical index to the patient monitor; and by the patient monitor:

determining whether communication with the one or more processors is available or not available;

responsive to determining that communication with the one or more processors is not available, temporarily processing at least the first and second sensor data locally at the patient monitor; and responsive to determining that communication with the one or more processors is available, communicating at least the first and second sensor data to the one or more processors.

12. The physiological monitoring method according to claim 11 further comprising:

causing display of the medical index on at least one of the patient monitor or a smart cellular telephone.

13. The physiological monitoring method according to claim 12, wherein the medical index includes an indication of at least one of: dehydration, renal insufficiency, over hydration, gastrointestinal bleeding, or congestive heart failure exacerbation.

14. The physiological monitoring method according to claim 13 further comprising:

by the one or more processors executing program instructions:

determining that required parameters for deriving the medical index include the plurality of parameters, and that the plurality of parameters are available for deriving the medical index; and determining that most-recent parameter measurements associated with the plurality of parameters satisfy a time frame mismatch tolerance associated with the medical index.

15. The physiological monitoring method according to claim 14, wherein determining the trends and deriving the medical index are performed in response to determining that most-recent parameter measurements associated with the plurality of parameters satisfy the time frame mismatch tolerance associated with the medical index.

16. The physiological monitoring method according to claim 15 further comprising:

by the one or more processors executing program instructions:

in response to determining that the most-recent parameter measurements associated with the plurality of parameters do not satisfy the time frame mismatch tolerance:

not deriving the medical index; and causing the at least one of the patient monitor or the smart cellular telephone to not display the medical index.

17. The physiological monitoring method according to claim 16, wherein causing the at least one of the patient monitor or the smart cellular telephone to not display the medical index further includes causing the at least one of the patient monitor or the smart cellular telephone to display dashes in a location on the monitor where the medical index otherwise would be displayed.

18. The physiological monitoring method according to claim 11, wherein the plurality of parameters include at least one of: hemoglobin (Hgb), blood urea nitrogen (BUN), creatinine (Cr), plethysmograph variability index (PVI), blood pressure (BP), total cholesterol (Chol), high-density lipoprotein (HDL), Chol/HDL, triglycerides (Trig), blood-constituents, oxygen saturation ($SpO_2$), respiration rate (RR), temperature, heart rate (HR), or electrocardiogram (ECG).

* * * * *